United States Patent [19]
Levine et al.

[11] Patent Number: 5,647,871
[45] Date of Patent: Jul. 15, 1997

[54] ELECTROSURGERY WITH COOLED ELECTRODES

[75] Inventors: Andy H. Levine, Newton Centre; John C. Meade, Walpole; Philip R. Lichtman, Newton, all of Mass.

[73] Assignee: MicroSurge, Inc., Needham, Mass.

[21] Appl. No.: 402,881

[22] Filed: Mar. 10, 1995

[51] Int. Cl.$^6$ ................................................. A61B 17/39
[52] U.S. Cl. ............................ 606/45; 606/48; 606/49; 606/51
[58] Field of Search ......................... 606/41, 42, 45, 606/46, 48–52; 607/105

[56] References Cited

U.S. PATENT DOCUMENTS

| | | | |
|---|---|---|---|
| 3,496,942 | 2/1970 | Shipley | 607/105 |
| 3,991,764 | 11/1976 | Incropera et al. | 128/303.1 |
| 4,202,336 | 5/1980 | van Gerven | 128/303.1 |
| 4,532,924 | 8/1985 | Auth et al. | 128/303.17 |
| 4,674,499 | 6/1987 | Pao | 128/303.14 |
| 4,931,047 | 6/1990 | Broadwin et al. | 606/45 |
| 5,171,311 | 12/1992 | Rydell et al. | 606/48 |
| 5,197,963 | 3/1993 | Parins | 606/46 |
| 5,282,799 | 2/1994 | Rydell | 606/48 |
| 5,318,589 | 6/1994 | Lichtman | 606/205 |
| 5,334,193 | 8/1994 | Nardella | 606/41 |
| 5,342,357 | 8/1994 | Nardella | 606/40 |
| 5,348,554 | 9/1994 | Imran et al. | 607/105 |

FOREIGN PATENT DOCUMENTS

| | | | |
|---|---|---|---|
| 120788 | 1/1946 | Australia | 606/49 |
| 480639 | 4/1992 | European Pat. Off. | 606/49 |

OTHER PUBLICATIONS

Brochure on Seitzinger Tripolar™ Cutting Forceps, Cabot Technology Corp., 1994, consisting of three pages.

Holman, J.P., *Heat Transfer*, Fourth Edition, McGraw–Hill Book Company, pp. 464–467.

Hoffmann, E., et al., "Temperature–controlled radiofrequency catheter ablation of AV conduction: first clinical experience," *European Heart Journal*, 14:57–64, (1993).

Bart, S.F., et al., "The Mechanism of Electrosurgical Coagulation: Steam Evolution Versus Dielectric Breakdown," *IEEE*, pp. 297–300, (1985).

Neiman, T.S., et al., "Thermal Characterization of Electrosurgery," *Biomat., Med. Dev., Art. Org.*, 11(1) :93–101, (1983).

*Primary Examiner*—Lee S. Cohen
*Attorney, Agent, or Firm*—Hamilton, Brook, Smith & Reynolds, P.C.

[57] ABSTRACT

A cooled electrosurgical system includes an electrosurgical device having at least one electrode for applying electrical energy to tissue. In one embodiment, the electrode includes an internal cavity in which a cooling medium such as water is contained. The internal cavity is closed at the distal end of the device such that the cooling medium is contained within the electrode at the surgical site such that the cooling medium does not contact the tissue being treated.

12 Claims, 11 Drawing Sheets

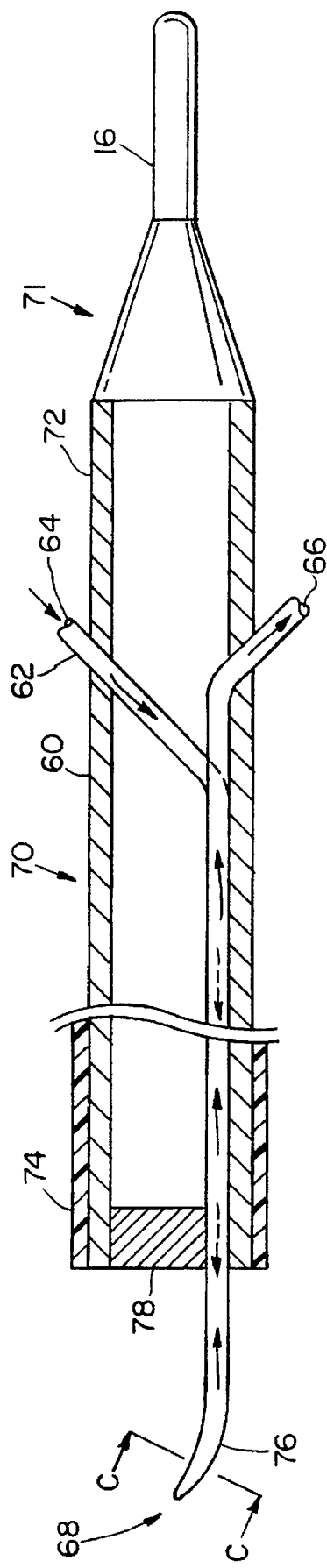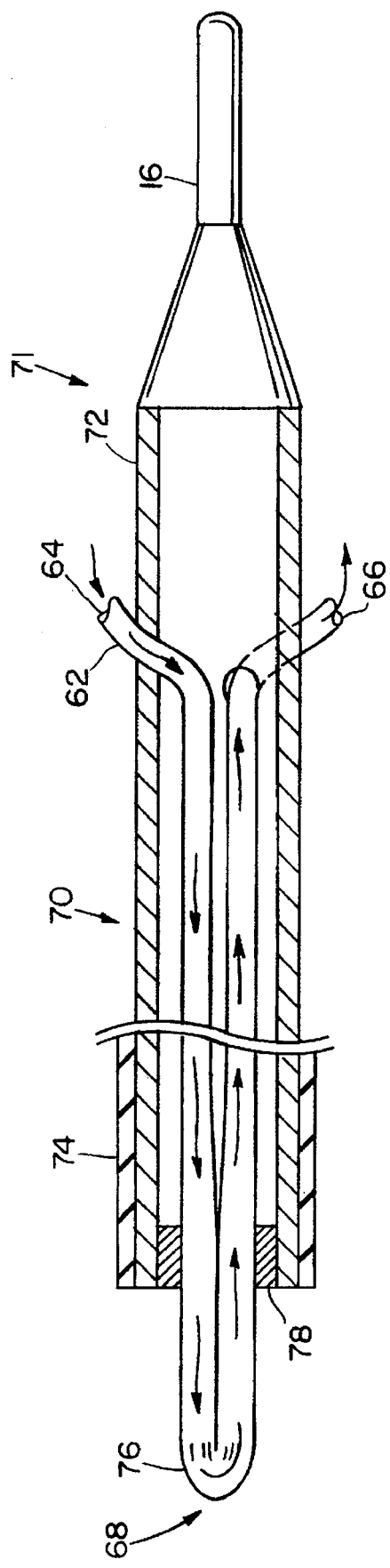
FIG. 3A
FIG. 3B

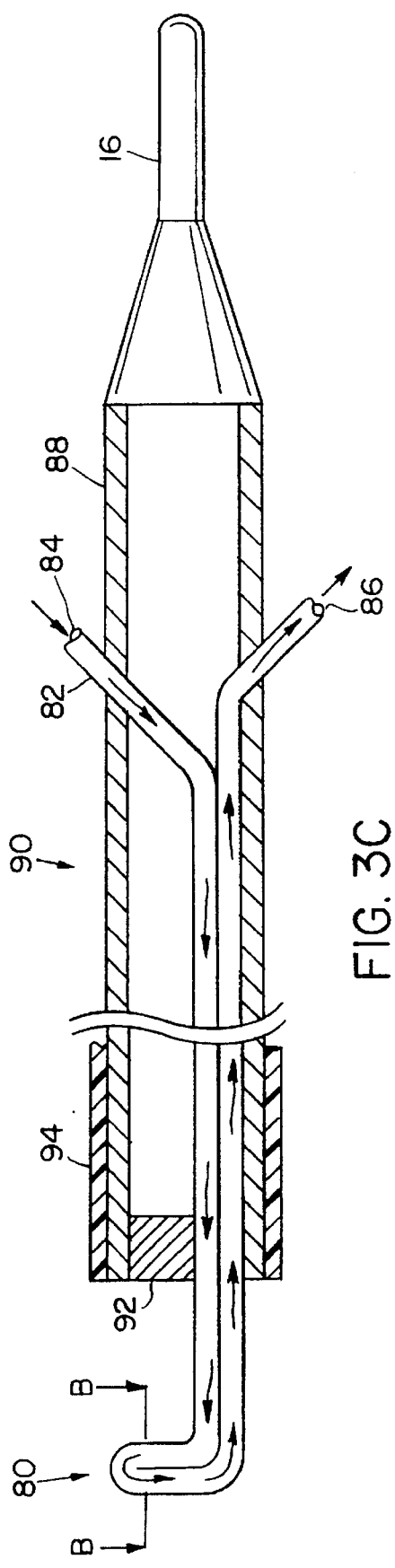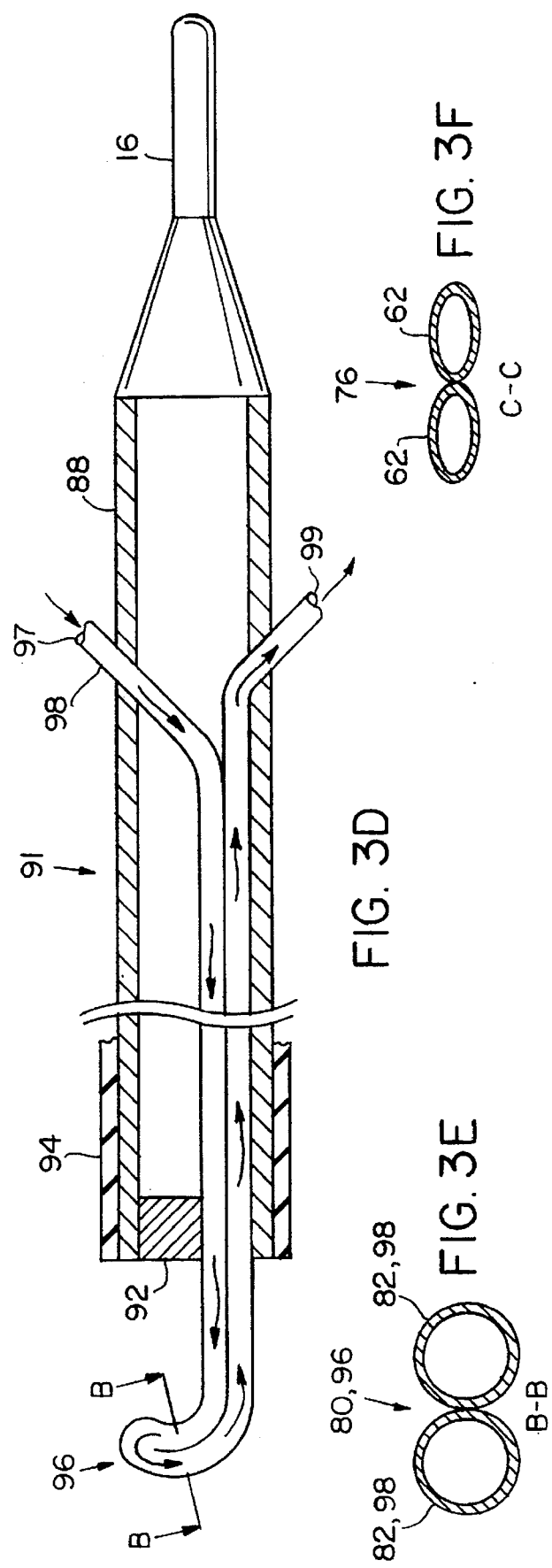

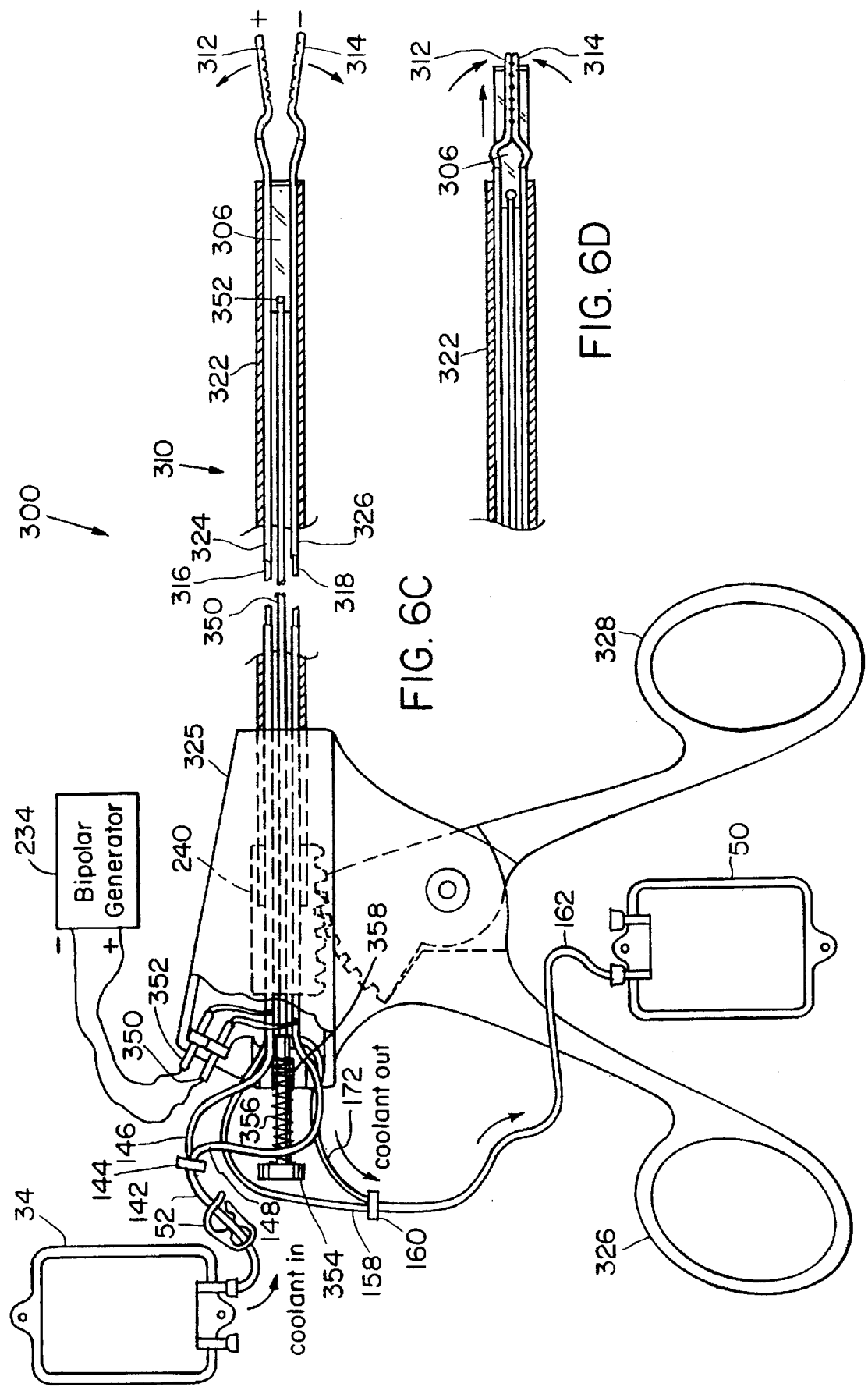

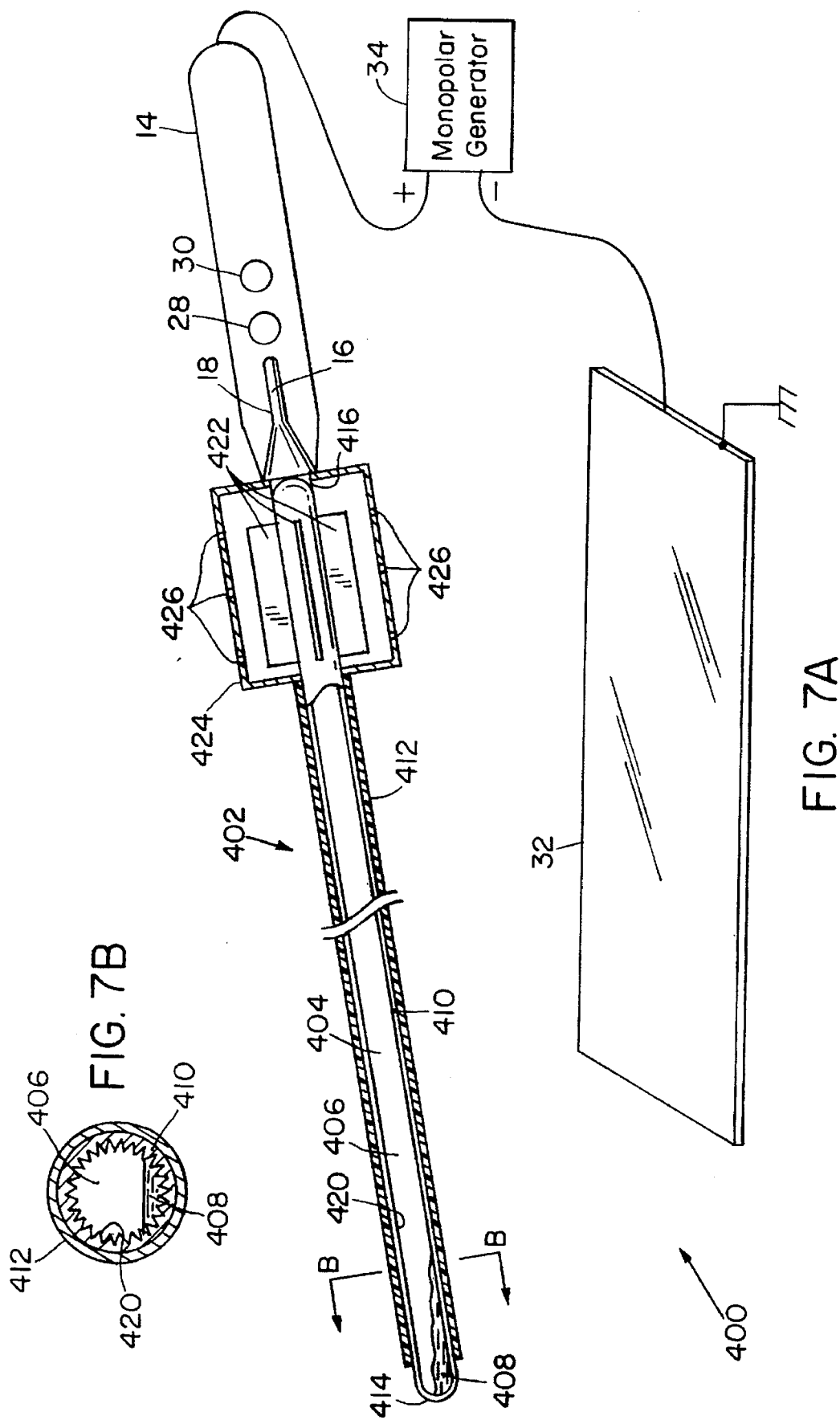

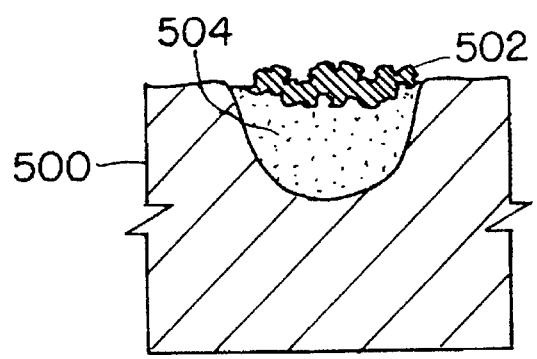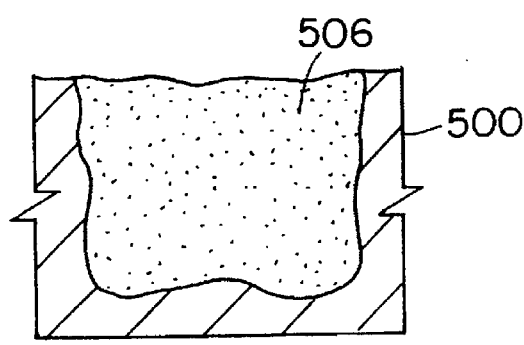
FIG. 8A  FIG. 8B
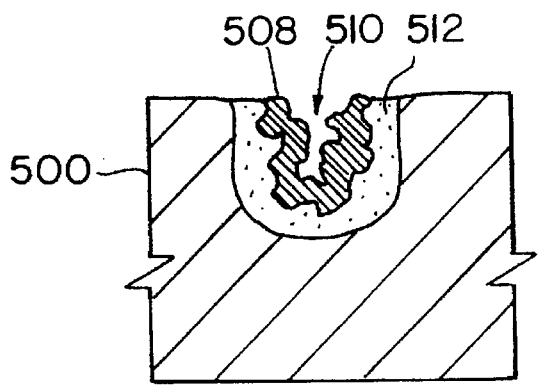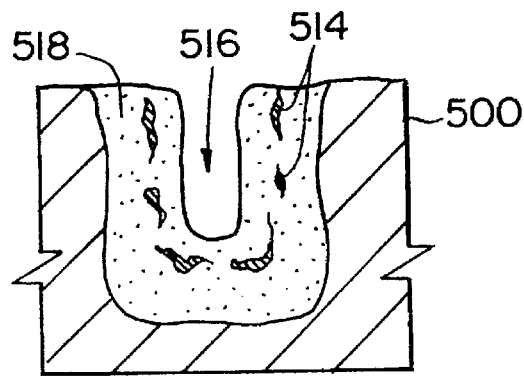
FIG. 9A  FIG. 9B

ELECTROSURGERY WITH COOLED ELECTRODES

BACKGROUND OF THE INVENTION

Electrosurgery is commonly used to cauterize, cut and/or coagulate tissue. In typical electrosurgical devices, RF electrical energy is applied to the tissue being treated. Local heating of the tissue occurs, and, depending upon the waveform of the applied energy, the desired effect is achieved. By varying the power output and the type of electrical waveform, it is possible to control the extent of heating and, thus, the resulting surgical effect. For example, a continuous sinusoidal waveform is best suited for cutting, while a waveform having periodically spaced bursts of a partially rectified signal produces coagulation.

In bipolar electrosurgery, the electrosurgical device includes two electrodes. The tissue being treated is placed between the electrodes, and the electrical energy is applied across the electrodes. In monopolar electrosurgery, the electrical excitation energy is applied to a single electrode at the surgical site, and a grounding pad is placed in contact with the patient. The energy passes from the single monopolar electrode through the tissue to the grounding pad.

While tissue heating is the mechanism by which the various surgical treatments are realized, it can also cause various obstacles to optimum procedure performance. For example, the heat causes tissue fluids to evaporate. As the tissue is desiccated, the electrical resistance of the tissue increases, making it increasingly more difficult to supply adequate power to the tissue. Eventually, the resistance rises to such a high level that it is impossible to continue the procedure. This is such a well-known and common problem in prior electrosurgical devices that surgeons have become accustomed to it and have tailored their procedures to minimize its effects. Typically, surgeons operate prior electrosurgical devices at a very low power level. This prevents the electrode and the adjacent tissue from becoming too hot too fast. Unfortunately, it also requires the surgeon to perform the procedure much more slowly than he would if he could operate the device at full power. As a result, the procedure takes much longer, requiring more operating room time and longer exposure of the patient to dangerous anesthetics.

Heating also causes charring of the tissue. Like desiccated tissue, charred tissue is of very high resistance. Therefore, as the surface of the tissue being treated becomes charred, it becomes difficult, and eventually impossible, to continue delivering power to the tissue as desired. Once again, to avoid the problem, surgeons perform procedures much more slowly than is desirable.

Electrosurgical procedures are also hindered by adherence of tissue to heated electrodes. During electrosurgery, the heated tissue tends to transfer heat to the electrodes. As an electrode becomes hot, tissue tends to stick to it, resulting in various complications. First, the tissue stuck to the electrode can have a high resistance and can therefore hinder delivery of power to the tissue. In prior devices, while performing a procedure, a surgeon must periodically remove the device from the patient and clean it before continuing. In addition, surgeons typically perform the procedure at low power to reduce tissue adherence and thus the frequency of cleanings.

Tissue sticking can also cause unnecessary bleeding. During electrosurgical procedures, the tissue being treated often heats the electrode such that, when the electrode is removed from the tissue, a portion of the tissue sticks to the electrode and is torn away, which likely results in bleeding. Thus, as the surgeon is attempting to cauterize in order to stop bleeding, he is actually causing more bleeding. He must therefore make repeated attempts to cauterize the area, first cauterizing, then tearing away tissue, then recauterizing the torn tissue, etc. Once again, in an attempt to alleviate the problem, surgeons will typically operate at low power, resulting in a procedure requiring much more time to complete than is desirable.

Another problem caused by heated electrodes is the creation of steam and smoke in the proximity of the surgical site. As a result, the surgeon's visibility is reduced, and he must periodically interrupt the procedure to allow the steam or smoke to dissipate.

It has been recognized that cooling the surgical site during electrosurgery would be desirable. In response, systems have been developed which flush the surgical site with fluid during surgery. However, this results in much more steam being created at the surgical site and the associated reduction in visibility. Also, the fluid introduced at the site must be aspirated as the procedure is performed.

SUMMARY OF THE INVENTION

The present invention is directed to an electrosurgical device and system and a method of electrosurgery in which electrosurgical electrodes are cooled. The device of the invention includes at least one electrode for applying the required electrical energy to tissue at a surgical site. During surgery, an internal cavity within the electrode contains a cooling medium such as water. The cooling medium is contained within the electrode at the surgical site such that it does not flow into the site.

The present invention is applicable to monopolar electrosurgery in which the device includes a single electrode and bipolar electrosurgery in which the device includes two electrodes, each of which contains the cooling medium. The invention is also applicable to any of the various electrosurgical procedures, including electrocautery, cutting and coagulation. In one embodiment, the electrosurgical device is an endoscopic device and can be inserted into a patient through a cannula. In another embodiment, the device is used in open surgical procedures.

In a preferred embodiment, the cooling medium is circulated through the cavity within the electrode. In that embodiment, the cavity is open at the proximal end of the device. The cooling medium enters the device through an inlet port, flows within the cavity to the distal end of the device and returns back to the proximal end of the device where it exits the device through an outlet port. In a preferred embodiment, the cooling medium such as water is provided from a fluid source bag or bottle suspended at some height above the device. The fluid flows by gravity out of the source bag through tubing to the inlet port of the electrosurgical device. The fluid exiting the device at the outlet port flows through outlet tubing to a collection bag or bottle. Hence, the electrode is cooled by a closed circulation system including the two bags, the tubing and the cavity or lumen within the electrode.

In another embodiment, the cooling fluid is pumped through the electrode by a circulation pump. In one embodiment, a source bag and collection bag are used as in the gravity-feed embodiment. However, a peristaltic roller pump is added to periodically squeeze a flexible fluid inlet tube to pump the cooling fluid through the electrosurgical device to the collection bag. Alternatively, a circulation pump can pump the fluid from a fluid reservoir into the device. The fluid circulates through the device and returns to the reservoir. The reservoir may be cooled such as by fins and/or blowers to remove heat from the system.

In another embodiment, instead of circulating the cooling medium through the electrodes, each electrode is configured as a heat pipe heat transfer device. That is, the electrode is closed at both its proximal and distal ends. The cavity within each electrode is evacuated and contains a liquid cooling medium such as water. When the distal end of an electrode contacts tissue heated by the electrosurgical procedure, the cooling medium inside the electrode evaporates, filling the internal cavity with vapor. At the proximal end of the electrode, the vapor condenses, and the resulting liquid flows back toward the distal end of the device via a wick. Heat is thus carried away from the distal end to cool the electrode at the surgical site. At the proximal end of the electrode, a heat exchanger in the form of external heat conductive fins may be used to carry heat away from the device.

In another embodiment, a solid electrode is used to apply the electrical energy at the surgical site. A heat exchanger in the form of heat conductive fins is formed at the proximal end of the electrode. In either this embodiment or the heat pipe embodiment, the heat exchanger at the proximal end of the electrode carries more heat away from the distal end of the electrode than an electrode without the heat exchanger inherently would carry away.

The present invention provides numerous advantages over prior electrosurgery devices, systems and methods. With a cooled electrode, desiccation and charring of the tissue adjacent to the electrode is reduced. As a result, the resistance of the tissue remains at a level low enough to allow efficient delivery of power to the tissue. Depth of penetration of the treatment is greatly increased. In addition, the surgeon need not operate the device at a low power level. In fact, the device can be operated at full power in most situations. This results in a much quicker and more efficient procedure. Substantial reductions in surgeon time and time of exposure to anesthesia are realized.

The cooled electrode of the invention also substantially reduces adherence of tissue to the electrode. The drawbacks of repeated periodic cleanings and inadvertent bleeding are virtually eliminated.

The use of a cooled electrode also substantially reduces smoke at the surgical site. Consequently, the surgeon's visibility is substantially improved.

Containing the cooling medium within the electrode also provides advantages. Because the fluid does not flood the surgical site, the added aspiration required in other systems is eliminated. Also, the additional steam caused by the boiling cooling fluid is eliminated.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3A is a schematic cross-sectional view of a cooled monopolar electrosurgical probe in accordance with the present invention having a spatula electrode.

FIG. 3B is a schematic cross-sectional view of the monopolar electrosurgical probe of FIG. 3A rotated 90°.

FIG. 3C is a schematic cross-sectional view of a cooled monopolar electrosurgical probe in accordance with the present invention having an L-hook electrode.

FIG. 3D is a schematic cross-sectional view of a cooled monopolar electrosurgical probe in accordance with the present invention having a J-hook electrode.

FIG. 3E is cross-sectional view of the monopolar electrodes of FIGS. 3C and 3D taken along lines B—B of FIGS. 3C and 3D.

FIG. 3F is a cross-sectional view of the monopolar spatula electrode of FIG. 3A taken along line C—C of FIG. 3A.

FIG. 6C is a schematic illustration of a cooled bipolar electrosurgical system in accordance with the present invention using the device of FIGS. 6A and 6B.

FIG. 6D is a schematic cross-sectional view of the distal end of the device of FIGS. 6A–6C shown with the cutting blade in the extended position.

FIG. 7A is a schematic illustration of an alternative embodiment of a cooled monopolar electrosurgical system in accordance with the present invention.

FIG. 7B is a schematic cross-sectional view of the monopolar electrosurgical probe of FIG. 7A taken along line B—B of FIG. 7A.

FIGS. 8A and 8B are conceptual drawings illustrating the effects on tissue of an electrosurgical coagulation procedure using non-cooled and cooled electrodes.

FIGS. 9A and 9B are conceptual drawings illustrating the effects on tissue of an electrosurgical cutting procedure using non-cooled and cooled electrodes.

DETAILED DESCRIPTION OF THE INVENTION

Figure 1:
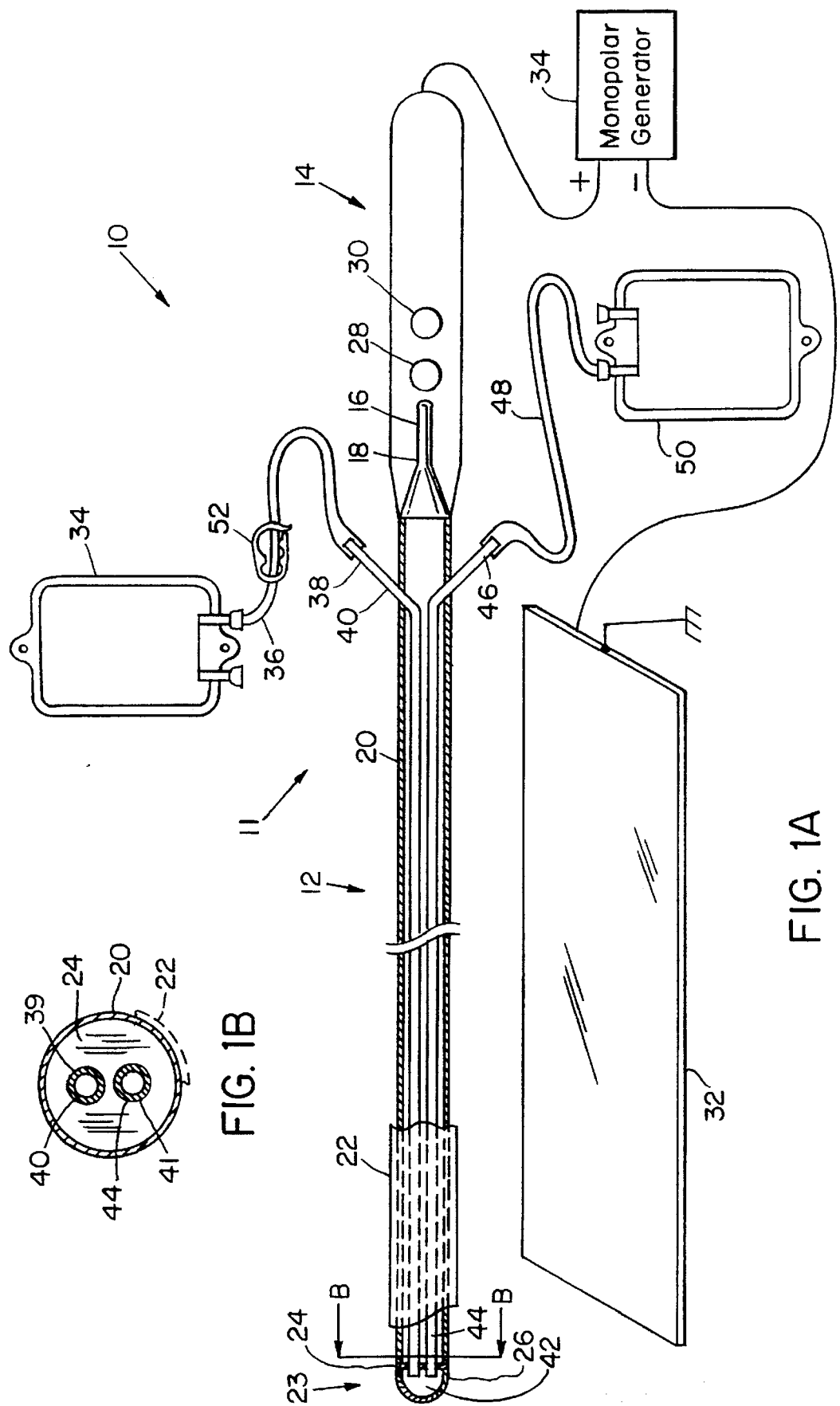
FIG. 1A is a schematic illustration of a cooled monopolar electrosurgery system in accordance with the present invention.
FIG. 1B is a schematic cross-sectional view of the cooled monopolar electrosurgical device of FIG. 1A taken along line B—B of FIG. 1A.

FIG. 1A is a schematic diagram of a cooled monopolar electrosurgery system 10 in accordance with the present invention. The system 10 includes an electrosurgical device 11 which includes an electrosurgical probe 12 connected at its proximal end to a standard electrosurgical control pencil 14. A male conductive plug 16 on the proximal end of the probe 12 is inserted and retained within a female conductive receptacle 18 at the distal end of the pencil 14. The probe 12 includes a conductive outer sleeve 20 in electrical contact with the connector 16. The sleeve 20 is covered with an insulating cover 22 which extends from the proximal end of the probe 12 to a location close to its distal end 23. A conductive spacer 24 is attached by soldering or welding or other known means to the distal end of the conductive sleeve 20. A conductive ball end or ball cap 26 is attached by soldering or welding or other known means to the conductive spacer 24.

Application of electrical energy to tissue is controlled by the electrosurgical pencil 14. The positive output of a monopolar generator 34 is applied to the probe 12 via the pencil 14. The opposite polarity of the generator 34 is applied to the grounding pad 32. To activate the device, one of the pushbuttons 28, 30 is depressed, depending upon the desired procedure. Typically, one of the buttons 28 applies a coagulation waveform to the probe to coagulate tissue while the other button 30 causes a cutting waveform to be applied to the tissue.

During an electrosurgical procedure, the patient is typically maintained in contact with the grounding pad 32, and the distal end 23 of the probe 12 is inserted into the patient and is maneuvered to a position adjacent to the tissue being treated. One of the pushbuttons 28, 30 is pressed to apply the positive polarity of the desired waveform to the tissue via the ball end electrode 26. The resulting current passes through the tissue to the grounding pad 32.

In the embodiment of FIG. 1A, the ball end electrode 26 is cooled by circulating a cooling fluid such as water through the probe 12. The fluid is contained within a source bag 34 suspended above the device 11. The fluid flows out of the bag 34 through tubing 36 and into the probe 12 at an inlet port 38 of an inlet tube 40. The fluid flows toward the distal end 23 of the probe 12 until it flows out of the distal end of the tube 40 into a cavity 42 formed by the ball end 26 and the spacer 24. The fluid then flows back toward the proximal end of the probe 12 in a second tube 44. The fluid exits the probe 12 through an output port 46 in the tube 44 and is carried by tubing 48 to a second collection bag 50. The collection bag 50 can be located below the device 11, such as on the floor of the operating room. The clamp 52 is used to control the fluid flow rate or to completely stop the flow of fluid where electrode cooling is not required.

The conductive spacer 24 at the distal end 23 of the probe 12 seals the cavity 42 from the remainder of the interior of the probe 12. FIG. 1B is a cross-sectional view of the probe 12 taken at line B—B of FIG. 1A. The outside diameter of spacer 24 is sealed to the inside diameter of the sleeve 20 by soldering or welding or other known electrically conductive sealing means. The inlet tube 40 is sealed within a hole 39 in the spacer 24, and the outlet tube 44 is sealed within a hole 41 in the spacer 24 by welding, soldering, etc.

It has been shown in the literature that many of the effects caused by heated electrodes can be avoided if the temperature at the electrode-tissue interface is maintained below a temperature of about 80° C. (See "Temperature-Controlled Radio Frequency Catheter Ablation of AV Conduction: First Clinical Experience," by Hoffmann et al., *European Heart Journal* (1993) 14, pages 57–64.) The present invention can maintain that electrode temperature during any of the various procedures performed. The temperature can be controlled by varying the fluid flow rate through the system 10 using the adjustable clamp 52 on the inlet tubing 36 as shown in FIG. 1A or on the outlet tubing 48. It has been shown that an appropriate electrode temperature can be maintained to eliminate the effects of electrode heating by using a flow rate between about 10 and 20 cc/min.

Typically, the bags 34 and 50 are available in one-liter and three-liter volumes. Using a three-liter bag, at a flow rate of 10 cc/min, a single bag can be used continuously to service a five-hour surgical procedure. However, even if the source bag 34 is completely drained, the positions of the two bags 34, 50 can be switched such that the collection bag 50 serves as the source bag, and the original source bag 34 serves as a collection bag. This can be done relatively quickly without interrupting the procedure.

Figure 2:
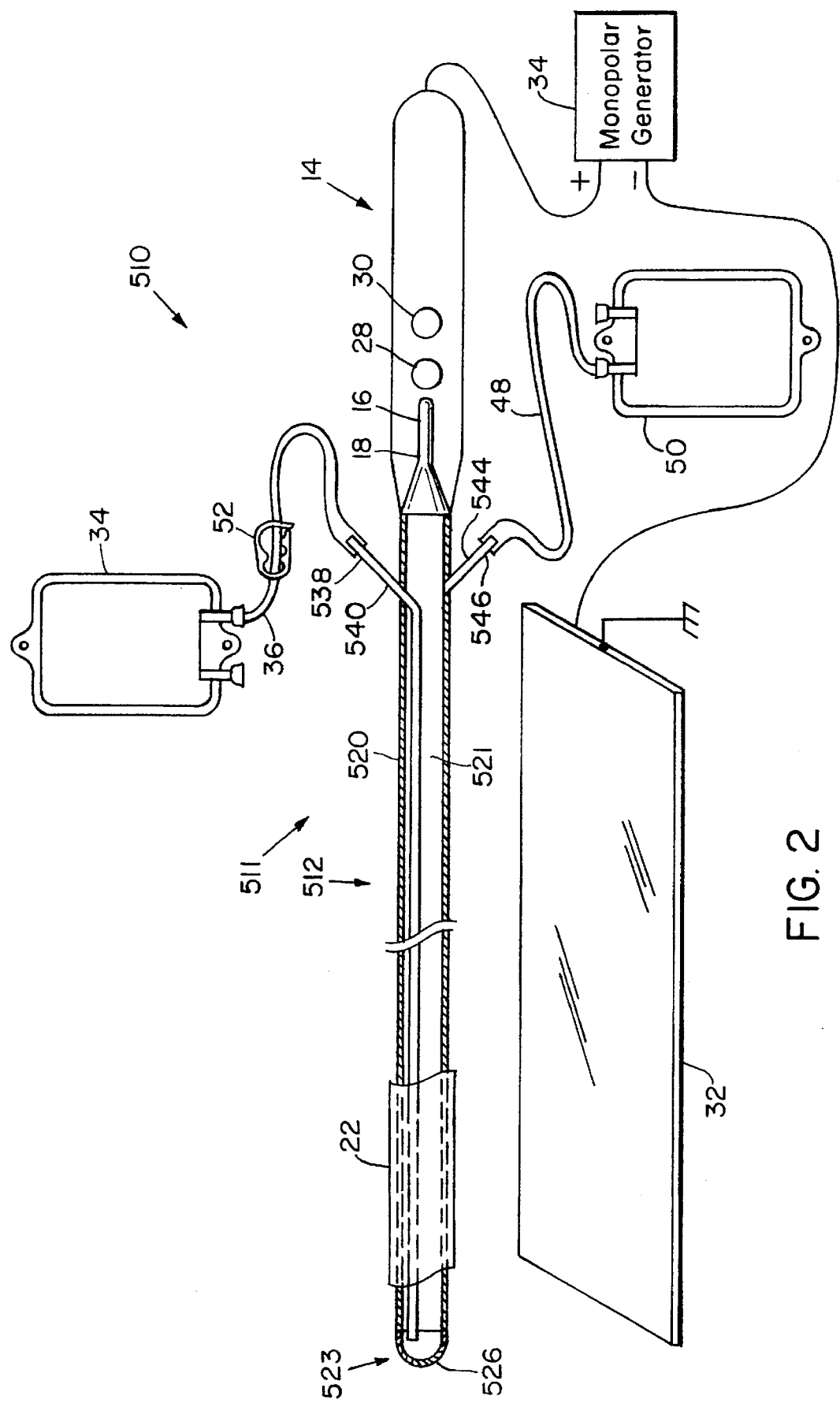
FIG. 2 is a schematic illustration of an alternative embodiment of a cooled monopolar electrosurgery system in accordance with the present invention.

FIG. 2 is a schematic illustration of an alternative embodiment 510 of a cooled monopolar electrosurgery system using a monopolar electrosurgical device 511 in accordance with the present invention. The system 510 is identical to the system 10 described above except for the means by which the cooling fluid is circulated through the monopolar electrosurgical probe 512. In the embodiment of FIG. 2, the cooling fluid is carried by a single tube 540 from the inlet port 538 of the probe 512 to the distal end 523 of the device. The fluid leaving the tube 540 at the distal end 523 cools the ball end electrode 526 of the device. Unlike the previously described embodiment, in the probe 512, the interior of the ball end electrode 526 is not isolated from the interior 521 of the sleeve 520. The ball end 526 is directly attached to the distal end of the sleeve 520, without an intervening conductive spacer, as is used in the previously described embodiment. Hence, the interior 521 of the probe 512 is flooded with the cooling fluid. The fluid flows out of the probe 512 through outlet tube 544 to the outlet port 546. As in the previously described embodiment, the fluid is carried into the collection bag 50 by an outlet tube 48.

In another embodiment of the monopolar electrosurgical device, the electrode is formed from a single conductive tube which also serves to circulate the cooling fluid within the device. Various configurations of this embodiment are shown in FIGS. 3A–3F. FIGS. 3A and 3B are two views of a monopolar electrosurgical probe 70 in accordance with the invention having a spatula monopolar electrode 76. FIG. 3B is shown rotated 90° relative to FIG. 3A about the longitudinal axis of the probe 70. The probe 70 includes a male conductive connector 16 electrically connected to an outer sleeve 72. The sleeve 72 is covered by an insulating cover 74 out to the distal end of the sleeve 72.

A single conductive tube 62 extends from near the proximal end 71 of the probe 70 out to the distal end 68 of the probe 70 where it is shaped to form the spatula electrode 76. The tube 62 is maintained in electrical contact with the conductive sleeve 72 by a conductive spacer 78. The spacer 78 is soldered or welded to the inside of the conductive sleeve 72, and the conductive tube 62 is soldered or welded to the spacer 78 to ensure good electrical contact. Hence, when the electric potential from the monopolar generator 34 (not shown) is applied to the probe 70, the potential is applied to the tissue being treated at the spatula electrode 76.

The spatula electrode 76 is cooled by cooling fluid circulating through the conductive tube 62. The fluid enters the tube 62 at an inlet port 64 and travels distally within the tube 62 out to the spatula electrode 76. It returns to the proximal end of the probe 70 within the tube 62 where it exits the device at outlet port 66.

FIG. 3F is a cross-sectional view of the spatula electrode 76 taken at line C—C of FIG. 3A. It will be noted that the tube 62 is slightly flattened to achieve the curved spatula configuration of the electrode 76.

FIG. 3C is a schematic diagram of a monopolar electrosurgical probe 90 in accordance with the present invention having an L-hook monopolar electrode 80. This embodiment also includes a conductive outer sleeve 88 connected to the male power input connector 16. A conductive tube 82 carries the cooling fluid from an input port 84 at the proximal end of the probe 90 out to the L-hook electrode 80 at the distal end of the probe 90. The tube 82 carries the cooling fluid back to the proximal end of the probe 90 where it exits the probe 90 at outlet port 86. A conductive spacer 92 is attached by soldering or welding to the inside of the conductive sleeve 88, and the conductive tube 82 is attached to the conductive spacer 92 and the inside of the sleeve 88 such that the electrical potential applied at connector 16 is applied to the tissue at the L-hook electrode 80.

FIG. 3D is a schematic diagram of a monopolar electrosurgical probe 91 in accordance with the present invention having a J-hook monopolar electrode 96. The J-hook probe 91 is the same as the L-hook probe 90 except for the shape of the J-hook electrode 96 at the distal end of the probe 91. The tube 98 is bent at the distal end to form the J-hook electrode 96. The cooling fluid enters the tube 98 at inlet port 97 and circulates out to the electrode 96 and back to the proximal end of the probe 91 where it exits the device at outlet port 99.

FIG. 3E is a cross-sectional diagram taken at lines B—B in FIG. 3C and FIG. 3D. It shows the substantially circular tubes 82 and 98 used to form the L-hook and J-hook electrodes 80 and 96, respectively.

Figure 4:
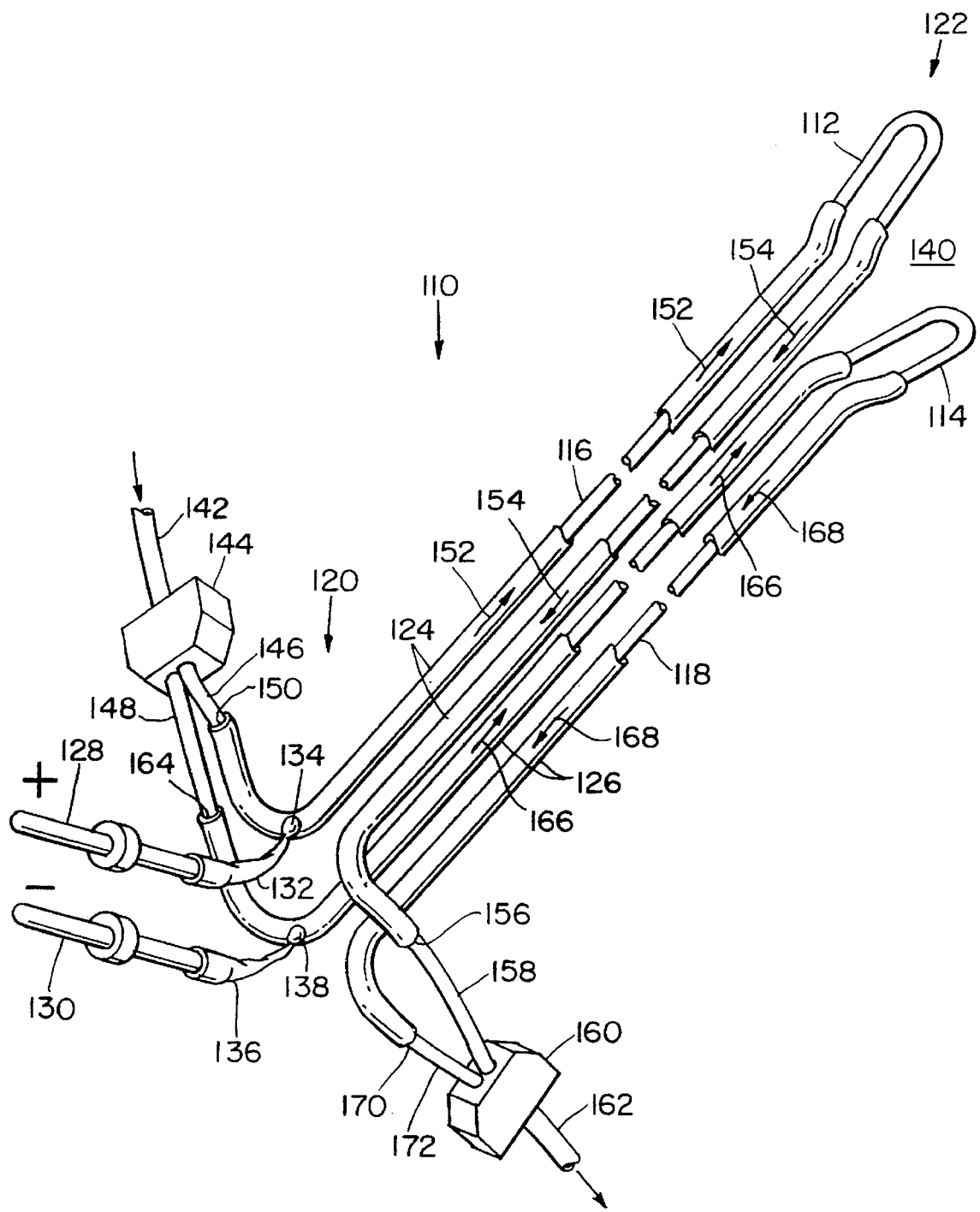
FIG. 4 is a schematic diagram illustrating the configuration of a cooled bipolar electrosurgical device in accordance with the present invention.

Having described a cooled monopolar electrosurgical device, system and method in accordance with the present invention, a cooled bipolar electrosurgical device, system and method will now be described in detail. FIG. 4 is a schematic illustration of the basic elements of a cooled bipolar electrosurgical device 110 in accordance with the present invention. Most of the supporting structure of the device 110 including the enclosure and mechanical actuation mechanism is not shown in FIG. 4. The drawing has been simplified to facilitate the description of the cooled bipolar electrosurgical electrodes of the embodiment of the invention.

The bipolar electrosurgical device 110 includes a pair of metallic conductive bipolar electrodes 112 and 114. In this embodiment, each electrode 112, 114 is formed from a continuous hollow metallic tube 116 and 118, respectively. Each tube 116, 118 is covered with an insulating cover which extends from near the proximal end 120 of the device 110 to near the electrodes at the distal end 122 of the device 110. Each cover 124, 126 is interrupted at the distal end 122 of the device 110 to expose its respective electrode 112, 114. In the embodiment of FIG. 4, conductive tube 116 is covered by insulator 124, and conductive tube 118 is covered by insulator 126.

In bipolar electrosurgery, tissue is treated by applying electrical energy across the tissue between electrodes 112 and 114 such that current flows through the tissue. To that end, each electrode 112, 114 is connected to an opposite polarity of a bipolar generator (not shown). The device 110 includes a positive, terminal 128 connected to the positive electrode 112 and a negative electrode 130 connected to the negative electrode 114. A conductive wire is connected to positive terminal 128 and runs within insulating cover 132 through insulating cover 124 and is attached by soldering or other known means to the conductive tube 116. Conductive covers 132 and 124 are joined at joint 134 such that no conductive materials are exposed. In similar fashion, a wire is attached to negative terminal 130 and runs within insulating cover 136 through the insulating cover 126 and is connected to conductive tube 118. Once again, the joint 138 is completely insulated. In operation, the positive terminal 128 of the device 110 is electrically coupled to the positive terminal of the bipolar generator, and the negative terminal 130 of the device 110 is electrically coupled to the negative terminal of the bipolar generator.

To electrosurgically treat a piece of tissue, the tissue is first located within the space 140 between the positive electrode 112 and negative electrode 114 of the device 110. Next, by a means to be described below, the two electrodes 112 and 114 are brought close together to squeeze the tissue. The bipolar electrical energy having the appropriate waveform is then applied via the terminals 128 and 130 across the electrodes 112 and 114. The resulting current flowing between the electrodes 112, 114 through the tissue treats the tissue as desired.

In the preferred bipolar electrosurgical device 110 of the invention, cooling fluid such as water flows through both electrodes 112 and 114 simultaneously. Fluid from a source bag (not shown) flows through inlet tube 142 and into a manifold device 144 which splits the fluid flow into two tubes 146 and 148. The fluid in tube 146 enters the conductive tube 116 of the device 110 at an inlet port 150. The fluid flows distally as indicated by arrows 152 until it reaches the electrode 112. The fluid loops back and flows proximally as indicated by arrows 154 and flows out of the device 110 at an outlet port 156 into an outlet tube 158. The fluid then flows through manifold 160 and into outlet tube 162. It then flows into a collection bag (not shown).

In similar fashion, fluid flows through inlet tube 148 and enters the conductive tube 118 at inlet 164. The fluid flows distally within tube 118 as shown by arrows 166. At the electrode 114, the fluid loops back and flows proximally as indicated by arrows 168 until it reaches the outlet port 170. The fluid at the outlet port 170 flows into an outlet tube 172 to the manifold 160 and into outlet tube 162 and finally into the collection bag (not shown).

Thus, as shown in FIG. 4, in one embodiment, the bipolar electrosurgical device 110 of the present invention is cooled by fluid in a closed circulation system. None of the cooling fluid is allowed to escape the system. Hence, during a procedure, no additional fluid need be aspirated from the surgical site.

Figure 5A:
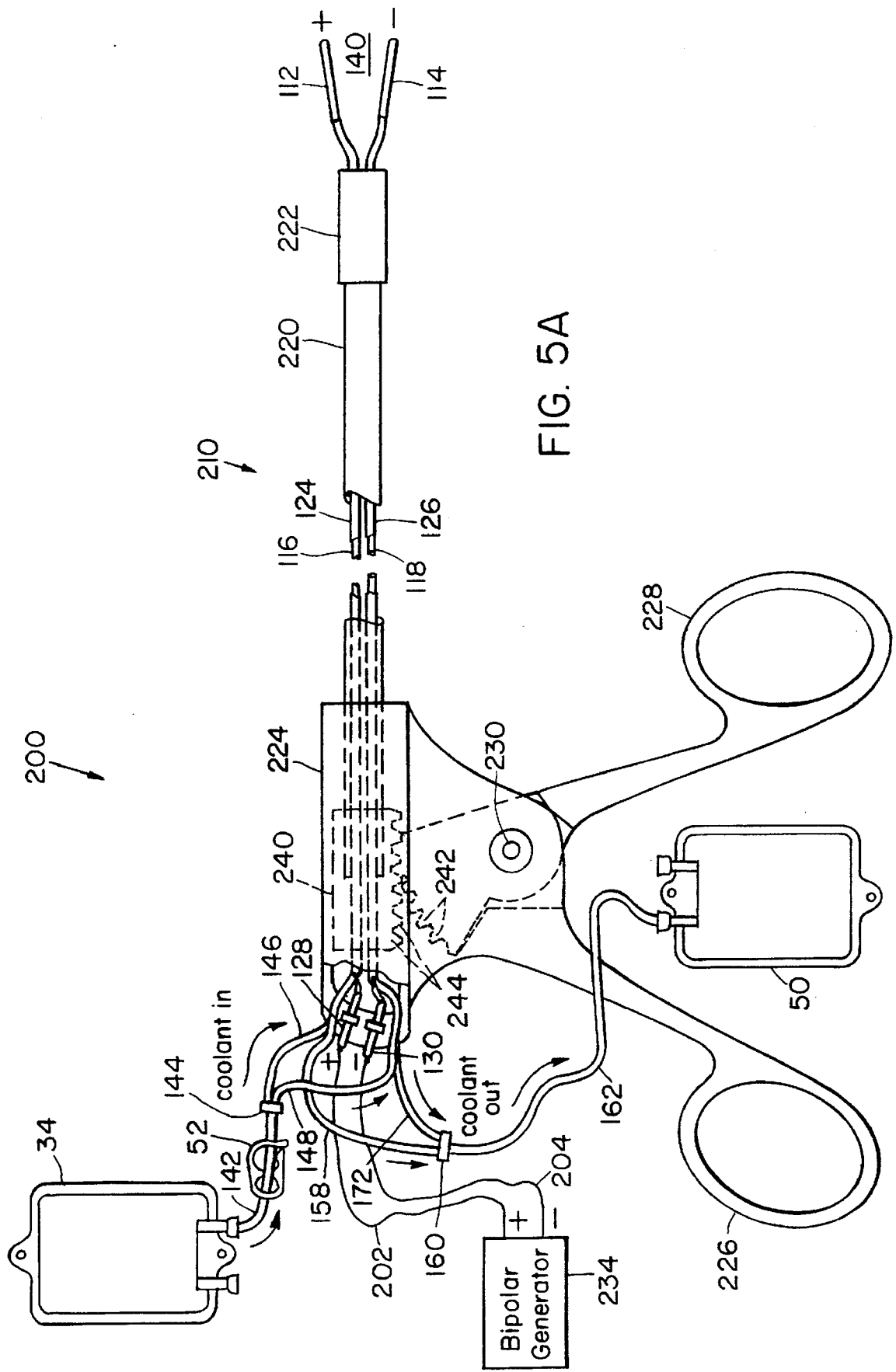
FIG. 5A is a schematic illustration of a cooled bipolar electrosurgical system in accordance with the present invention using a cooled bipolar electrosurgical grasper device.

FIG. 5A is a schematic diagram of a cooled bipolar electrosurgery system 200 in accordance with the present invention. The figure includes a side elevational schematic view of a bipolar electrosurgical device 210 in the form of a grasper instrument. The instrument 210 employs the cooled electrode configuration described above in connection with FIG. 4.

Figure 5B:
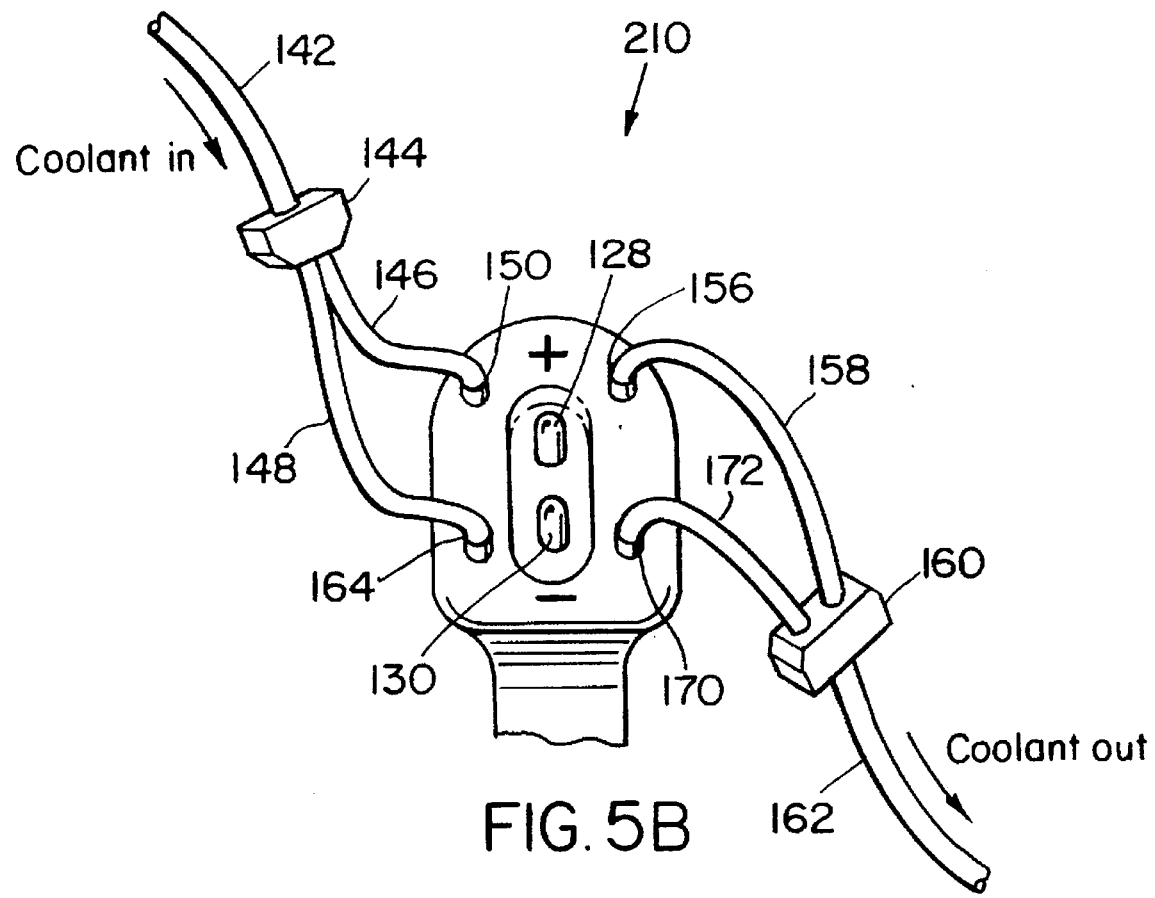
FIG. 5B is a schematic view of the proximal end of the cooled bipolar electrosurgical grasper device of FIG. 5A.

FIG. 5B is a schematic view of the proximal end of the cooled bipolar electrosurgical device 210 of FIG. 5A. Referring to FIGS. 5A and 5B, a source bag 34 of water or other cooling fluid is suspended above the instrument 210 such that the fluid is provided to the instrument 210 by gravity along a flexible tube 142. An adjustable clamp 52 is placed over the tube 142 such that the flow rate of fluid can be controlled. The fluid enters the manifold device 144 which splits the fluid into two inlet tubes 146 and 148. Fluid in tube 146 enters the device 210 at an inlet port 150 which is connected to the internal cavity or lumen within the hollow conductive tube 116. The fluid flows within tube 116 to the distal end of the device 210 where the tube 116 is looped to form the positive electrode 112. The fluid flows through the loop and back toward the proximal end of the device 210. It then exits the device 210 through the outlet port 156 into tube 158. The fluid flows into another manifold device 160 and then into outlet tube 162 and is collected by collection bag 50.

Likewise, the cooling fluid in tube 148 enters the device 210 through a second inlet port 164 and is coupled into the cavity within the conductive tube 118. The fluid flows down the tube 118 to the distal end of the device 210 where the tube 118 is shaped to form negative electrode 114. The fluid flows back along the tube 118 to the proximal end of the device 210 where it exits the device 210 through outlet port 170 and flows into tube 172. It then flows through manifold device 160 into tube 162 and is collected by the collection bag 50.

Electrical energy is provided to the electrodes 112 and 114 by a bipolar generator 234. The positive terminal of the generator 234 is coupled to the positive terminal 128 of the device 210 by means such as wire 202. The negative terminal of the generator 234 is connected to the negative terminal 130 of the device 210 by wire 204. The positive and negative terminals 128 and 130 are connected to the conductive tubes 116 and 118 as described above in connection with FIG. 4. In actual practice, the generator 234 is coupled to the device 210 through a switch which allows the surgeon to control application of electrical energy. The switch is typically mounted in a foot petal device on the floor of the operating room and is opened and closed by the surgeon using his foot.

As mentioned above, the device 210 of FIG. 5A is a grasper. As such, the electrodes 112 and 114 also act as controllable jaws which can be opened and closed to grasp the tissue being treated. The opening and closing of the jaws/electrodes 112, 114 is effected by longitudinal translation of an outer tube 220 relative to the jaws 112, 114. At the distal end of the device 210, the jaws 112, 114 are radially enclosed within a rigid sleeve 222 attached to the distal end of the tube 220. If the tube 220 is translated toward the distal end of the device relative to the jaws 112, 114, the sleeve 222 squeezes the jaws 112, 114 toward the closed position. If the tube 220 is made to slide in the proximal direction, the jaws 112, 114 open.

The grasper device 210 of the invention includes a rigid housing 224 integrally coupled to a thumb member 226 in which the surgeon inserts his thumb to control the device 210. A finger member 228, in which the surgeon inserts a finger, is pivotably connected to the housing 224 at a pivot point 230. The proximal end of the outer tube 220 is secured within a bore of the housing 224 to a gear rack member 240. The gear rack and, hence, the outer tube 220 are free to move longitudinally within the bore of the housing 224.

The tubes 116 and 118, covered with insulating covers 124 and 126, respectively, are held stationary relative to the housing 224. Gear teeth 242 integrally formed on the pivotable finger member 228 mesh with gear teeth 244 on the gear rack 240. As the finger member 228 pivots about the pivot 230, the gear rack 240 and the outer tube 220 are carried longitudinally relative to the housing 224. Since the tubes 116 and 118 are held stationary relative to the housing 224, the longitudinal movement of the outer tube 220 relative to the inner tubes 116 and 118 causes the jaws 112 and 114 to open and close. As the finger member 228 and thumb member 226 are pulled toward each other, the outer tube 220 moves toward the distal end of the device 210 to close the jaws 112 and 114. As the finger member 228 and thumb member 226 are spread apart, the outer tube 220 moves proximally to allow the jaws 112 and 114 to spring open. Further details of the grasper mechanism are provided in the commonly assigned U.S. Pat. No. 5,318,589, which is incorporated herein in its entirety by reference.

In operation, the cooled bipolar electrosurgical grasper 210 is operated by first spreading the finger member 228 and thumb member 226 to open the jaws/electrodes 112 and 114. The device 210 is then positioned to place tissue within the space 140 between the open jaws 112 and 114. Next, the finger member 228 and thumb member 226 are squeezed toward each other to close the jaws 112 and 114 over the tissue. The coolant valve 52 is then opened to allow coolant to flow through the device 210 and the electrodes 112 and 114. The required bipolar energy waveform is then applied at the electrodes 112 and 114 across the tissue. When the electrosurgical procedure is completed, the electrical energy is removed, and the finger member 228 and thumb member 226 are spread apart to open the jaws 112 and 114.

Figure 5C:
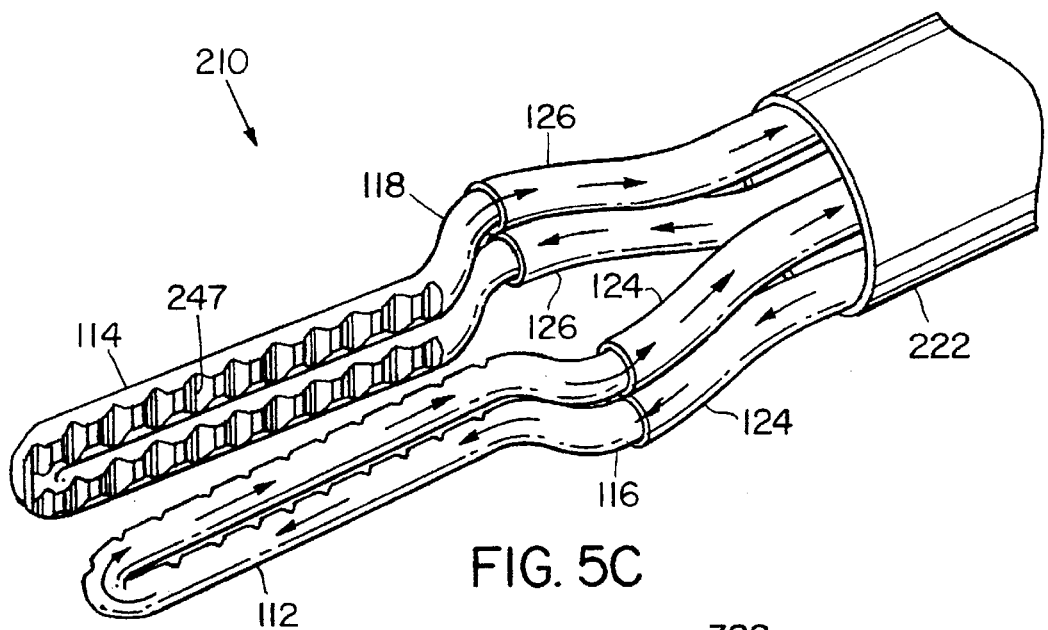
FIG. 5C is a schematic perspective view of the distal end of the cooled bipolar electrosurgical grasper device of FIG. 5A.

FIG. 5C is an expanded perspective view of the distal end of the bipolar electrosurgical grasper device 210 of the invention. As described above, the electrode 112 is formed from the conductive tube 116, and the electrode 114 is formed from the conductive tube 118. Tube 118 is covered with an insulating cover 126, and tube 116 is covered with an insulating cover 124. The insulation is removed from the tubes as required at the distal end to allow electrical conduction to take place between the electrodes 112 and 114 across the tissue being treated.

The direction of coolant flow within the tubes 116, 118 is illustrated by the arrows. However, it will be appreciated that the direction of flow is arbitrary. The flow directions can be altered by altering the fluid connections at the fluid inlet and outlet ports at the proximal end of the device 210. It will be noted that the jaws/electrodes 112 and 114 include grooves or serrations 247 to improve the device's grasping ability.

FIGS. 6A–6D depict a cooled bipolar electrosurgical grasper/cutting device 310 in accordance with the present invention. This device 310 is very similar to the grasper device 210 described immediately above. However, the device 310 includes an additional feature which allows it to cut tissue between the bipolar electrodes. The additional feature is an extendable blade 306 which can be caused to extend into the space between the arms of the electrodes to cut tissue between them.

Figure 6A:
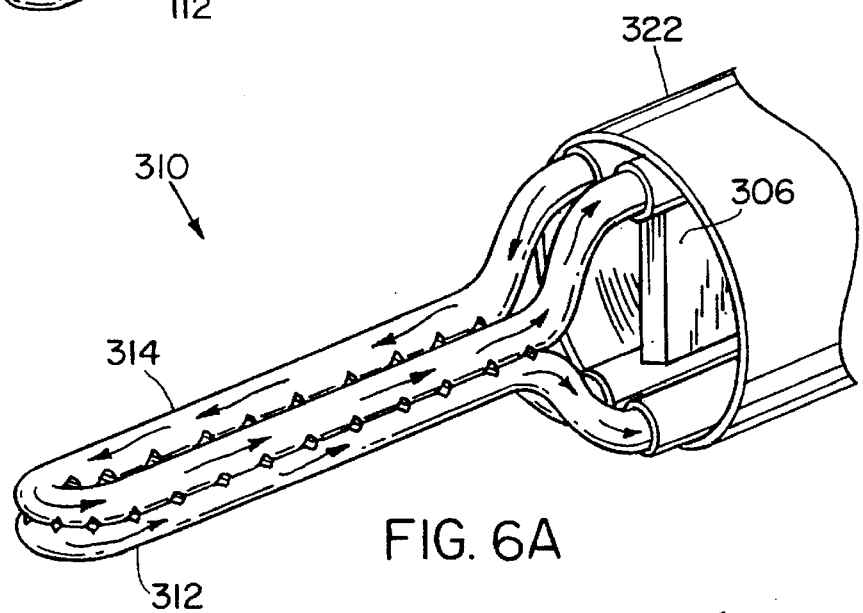
FIG. 6A is a schematic perspective view of the distal end of a cooled bipolar electrosurgical grasper device having a retractable cutting blade shown in the retracted position.
Figure 6B:
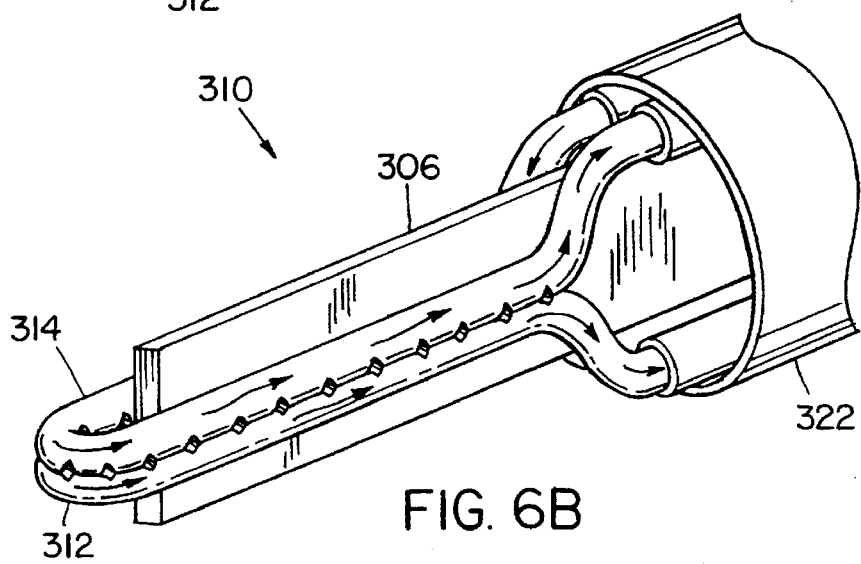
FIG. 6B is a schematic perspective view of the distal end of the device of 6A showing the cutting blade in the extended position.

FIGS. 6A and 6B are schematic perspective views of the distal end of the device 310. In both figures, the jaws/electrodes 312 and 314 are shown held closed by the outer sleeve 322. In FIG. 6A, the blade 306 is shown in the retracted position, pulled back inside the outer sleeve 322. In FIG. 6B, the blade is shown in the extended position in which it protrudes to the distal end of the device 310 between the arms of the closed jaws/electrodes 312, 314.

This device is useful in surgical procedures in which it is desired to cut a lumen, tube or vessel within a patient and seal the cut ends of the vessel in the same procedure. The jaws 312, 314 are closed over the vessel to be cut, and the electrical energy is applied across the electrodes to cauterize the vessel on opposite sides of the jaws 312, 314. Then, to ensure complete cutting of the vessel, the blade 306 is extended into the space between the arms of the jaws/electrodes 312, 314 to completely physically cut the tissue, resulting in a complete separation of the ends of the vessel.

FIG. 6C is a schematic illustration of a bipolar electrosurgery system 300 using the electrosurgical cutting device 310. The cutting device 310 is shown in a schematic side elevational view partially cut away. The system 300 is identical to the previously described system 200 except for the cutting blade feature added to the device 310. Hence, the cooling system is identical to that described above in connection with FIG. 5A.

The positive electrode 312 is formed at the distal end of the device 310 from the conductive tube 316, and the negative electrode 314 is formed from the conductive tube 318. Tube 316 is covered with insulating cover 324, and tube 318 is covered with insulating cover 326. Tube 316 is connected to the positive terminal 352 of the device 310, and tube 318 is connected to the negative terminal 350 of the device 310. The positive terminal 352 is coupled to the positive pole of the bipolar generator 234, and the negative terminal 350 is coupled to the negative pole of the generator 234. Once again, the device 310 is actually connected to the generator 234 through a foot petal switch to allow the surgeon to control application of the electrical energy to tissue.

The jaws/electrodes 312 and 314 are opened and closed as described above in connection with FIG. 5A. Finger member 328 is rotated relative to the stationary housing 325 and the integral thumb member 326. Gear rack 340, fixedly connected to the proximal end of the outer tube 322, slides back and forth longitudinally relative to the tubes 316 and 318. As the tube 322 slides toward the distal end of the driver 310, the jaws 312, 314 are pinched closed. As the tube 322 slides toward the proximal end of the device 310, the jaws 312, 314 spring open.

FIG. 6C shows the blade 306 in the retracted position. Movement of the blade 306 is controlled by a control arm 350 connected to the blade 306 at 352. The proximal end of the control arm 350 is fixed within a plunger 354. A coil spring 356 within a cavity 358 of the housing 325 biases the plunger 354 and, therefore, the control rod 350, toward the proximal end of the device 310 to bias the blade 306 to the retracted position. When the plunger 354 is pressed toward the proximal end of the device 310, the blade 306 is extended out the distal end of the outer tube 322 within the space between the jaws 312, 314. FIG. 6D shows the blade 306 in the extended position with the jaws 312, 314 closed.

In the embodiments of the electrosurgery system of the invention described above, the cooling medium is circulated through the electrodes by a closed gravity-feed circulation system. Other means of circulating the fluid through the electrode can also be used. For example, as previously described, a peristaltic pump can be used to pump the fluid from the source bag, through the electrode into the collection bag. Alternatively, a circulation pump can be used to circulate the fluid from a cooled reservoir through the device.

FIGS. 7A and 7B schematically depict another embodiment of a monopolar electrosurgical system 400 in accordance with the present invention. In this embodiment, the monopolar probe 402 employs a heat pipe heat transfer device 404 as the monopolar electrode. The heat pipe is a well-known heat transfer mechanism and is described in textbooks on heat transfer such as *Heat Transfer*, Fourth Edition, by J. P. Holman, McGraw-Hill, 1963, pp. 464–467, which is incorporated herein in its entirety by reference. FIG. 7B is a schematic cross-sectional view of the monopolar probe 402 taken along line B—B of FIG. 7A.

Referring to FIGS. 7A and 7B, the heat pipe 404 includes an internal cavity 406 which is sealed at both ends. The cavity 406 is partially evacuated and contains a heat transfer fluid such as water 408. The outer shell 410 is made of a conductive metallic material such as copper. The shell 410 is covered over most of its length by an insulating cover 412. The exposed distal end 414 of the heat pipe 404 is coated with a conductive non-toxic material such as gold.

The proximal end 416 of the heat pipe 404 is in conductive contact with the male connector 16 at the proximal end of the probe 402. As with the previously described monopolar instruments, the male connector 16 is inserted into the female receptacle 18 of the monopolar pencil 14. When electrical energy is applied to the male connector 16, it is conducted along the conductive outer shell 410 of the heat pipe 404 to the distal end 414 of the heat pipe 404. The distal end 414 serves as a ball-end monopolar electrode of the device.

In operation, the electrode 414 is placed adjacent to tissue being treated. At the same time, the patient is maintained in contact with the grounding pad 32. As in the previous embodiments, the monopolar pencil 14 controls application of the electrical energy. One of the pushbuttons 28 and 30 is depressed to apply the electrical energy to the tissue according to the desired tissue treatment. When one of the buttons is pressed, electrical energy from the monopolar generator 34 is applied across the ball-end electrode 414 and the grounding pad 32 to treat the tissue.

The heat pipe 404 of the probe 402 serves to cool the monopolar electrode 414. During operation, the distal end electrode 414 is heated by the tissue. In accordance with the well-known operation of the heat pipe heat transfer device 404, the water 408 within the cavity 406 of the heat pipe 404 evaporates, and the cavity 406 fills with vapor. The inner wall 420 of the heat pipe 404 serves as a wick, which, in one embodiment, takes the form of multiple grooves or slots distributed over the entire inner wall 420 of the outer shell 410. At the proximal end of the device, the vapor condenses, and the resulting liquid flows back to the distal end of the device via capillary action within the wick 420. Heat is thus carried away from the electrode 414 at the distal end of the device.

The proximal end of the heat pipe 404 includes a heat exchanger in the form of multiple radial heat conductive fins 422 attached to the outer shell 410 so as to conduct heat away from the heat pipe 404. A non-conductive enclosure 424 encloses the fins 422 as a safety precaution to prevent burning the surgeon's hands. The enclosure 424 includes multiple holes 426 to allow the heat to be dissipated.

In a preferred embodiment, the heat pipe used has a circular cross section with a diameter of approximately 5 mm. However, other configurations are possible and have been shown to be effective in eliminating the effects of electrode heating. For example, an oval cross-sectional heat pipe, such as part number 1861-4 produced by Noren Products Inc. of Menlo Park, Calif., has been shown to be effective. The device is oval shaped in cross-section having a minor diameter of 2.3 mm and a major diameter of 3.8 mm and an overall length of approximately 15 inches.

It will also be appreciated that the distal end of the heat pipe can be shaped to form any desired electrode shape such as the spatula, L-hook, and J-hook previously described. It will also be appreciated that the heat pipe configuration can also be used in bipolar instruments. The monopolar instrument is shown in FIGS. 7A and 7B for illustration purposes only and is not intended to be a limitation.

In another embodiment, the heat pipe 404 of FIG. 7A is replaced in the probe 402 with a solid conductive rod. The rod carries applied electrical energy from its proximal end to the electrode at its distal end located at the surgical site to treat tissue. The heat exchanger made of the radial conductive fins 422 attached to the proximal end of the rod causes heat to flow from the distal end of the rod to the proximal end of the rod to cool the electrode at the surgical site. Whether the solid rod or heat pipe is used, substantially more heat is removed from the electrode than would be removed by the inherent heat conduction of the devices without the heat exchanger.

FIG. 8A and 8B are schematic illustrations which compare the results of tissue coagulation procedures using a non-cooled electrode (FIG. 8A) and cooled electrode (FIG. 8B). In FIG. 8A, a non-cooled electrode has been used to treat a piece of tissue 500. Because the electrode was not cooled, a layer of charred tissue 502 is formed at the surface of the tissue 500. As a result, the depth of treated tissue 504 is severely limited. FIG. 8B shows the results of treatment with a cooled electrode. Since there is no layer of charred tissue, the depth of penetration is greatly increased and, hence, so is the depth of successfully treated tissue 506.

FIGS. 9A and 9B compare the results of a cutting operation using non-cooled (FIG. 9A) and cooled (FIG. 9B) electrodes. Referring to FIG. 9A, since the electrode is not cooled, a layer of charred tissue 508 is formed. As a result, the depth of cutting 510 and the depth of penetration of treated tissue 512 is severely limited. Referring to FIG. 9B, because the electrode is cooled, the amount of charring 514 is substantially reduced. As a result, the depth of cutting 516 as well as the depth of penetrated tissue 518 are increased.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. An electrosurgery system comprising:

an electrosurgical device having an electrode for applying electrical energy to tissue at a surgical site to heat and thus cut or stop bleeding of the tissue;

a cooling medium;

an internal cavity within the electrode for containing the cooling medium therein at the surgical site to cool the electrode; and a gravity-fed closed circulation system that circulates the cooling medium through the internal cavity, the closed circulation system comprising:

a first container providing the cooling medium by gravity to the internal cavity, and a second container collecting the cooling medium as it exits the internal cavity.

2. The electrosurgery system of claim 1 further comprising:

a second electrode for applying electrical energy to the tissue at the surgical site; and a second internal cavity within the second electrode for containing therein at the surgical site the cooling medium to cool the second electrode.

3. The electrosurgery system of claim 2 wherein the cooling medium is circulated through the second internal cavity.

4. The electrosurgery system of claim 1 wherein the cooling medium is water circulated at a flow rate of less than 20 cc/minute to maintain an electrode-tissue interface temperature of less than about 80° C.

5. The electrosurgery system of claim 1 wherein the electrosurgical device is a monopolar electrosurgical device with a single electrode.

6. The electrosurgery system of claim 1 wherein the electrosurgical device is a bipolar electrosurgical device.

7. The electrosurgery system of claim 1 further comprising a retractable cutting blade for cutting tissue.

8. An electrosurgery system comprising:

an electrosurgical device having an electrode for applying electrical energy to tissue to heat and thus cut or stop bleeding of the tissue; and a gravity-fed closed circulation system for circulating a cooling fluid within the electrosurgical device to cool the electrode, the gravity-fed closed circulation system comprising:

a first container providing the cooling fluid by gravity to the electrosurgical device; and a second container collecting the cooling fluid as it exits the electrosurgical device.

9. The electrosurgery system of claim 8 wherein the closed circulation system further comprises an internal cavity within the electrode through which the cooling fluid circulates at a flow rate of less than 20 cc/minute to maintain an electrode-tissue interface temperature of less than about 80° C.

10. The electrosurgery system of claim 8 wherein the electrosurgical device is a monopolar electrosurgical device with a single electrode.

11. The electrosurgery system of claim 8 wherein the electrosurgical device is a bipolar electrosurgical device.

12. A method of electrosurgery comprising:

applying electrical energy to tissue with an electrode at a surgical site to heat and thus cut or stop bleeding of the tissue; and cooling the electrode at the surgical site with a cooling medium contained within the electrode at the surgical site, said cooling comprising:

providing the electrode with an internal cavity that contains the cooling medium, and providing a gravity-fed closed circulation system connected to the electrode, the closed circulation system including a first container providing the cooling medium by gravity to the internal cavity and a second container collecting the cooling medium as it exits the internal cavity.

* * * * *

UNITED STATES PATENT AND TRADEMARK OFFICE
CERTIFICATE OF CORRECTION

PATENT NO. : 5,647,871
DATED : July 15, 1997
INVENTOR(S) : Andy H. Levine, John C. Meade and Philip R. Lichtman It is certified that error appears in the above-indentified patent and that said Letters Patent is hereby corrected as shown below:

In Claim 7, Column 14, line 15, after "tissue," insert ---engaged by the electrode---.

Signed and Sealed this

Twenty-third Day of September, 1997

Attest:

BRUCE LEHMAN

Attesting Officer

Commissioner of Patents and Trademarks